United States Patent
Thottathil et al.

(10) Patent No.: US 7,176,326 B2
(45) Date of Patent: Feb. 13, 2007

(54) β-LACTAMS, METHODS FOR THE PREPARATION OF TAXANES, AND SIDECHAIN-BEARING TAXANES

(75) Inventors: John K. Thottathil, Robbinsville, NJ (US); Ivan D. Trifunovich, Belle Mead, NJ (US); David J. Kucera, Warren, NJ (US); Wen-Sen Li, Lincroft, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/969,693

(22) Filed: Oct. 20, 2004

(65) Prior Publication Data

US 2005/0107605 A1 May 19, 2005

Related U.S. Application Data

(60) Continuation of application No. 10/006,599, filed on Dec. 5, 2001, now abandoned, which is a continuation of application No. 08/440,291, filed on May 12, 1995, now Pat. No. 6,350,887, which is a division of application No. 08/320,628, filed on Oct. 11, 1994, now abandoned, which is a continuation of application No. 08/033,598, filed on Mar. 19, 1993, now abandoned.

(51) Int. Cl.
- *C07D 305/00* (2006.01)
- *C07D 407/00* (2006.01)
- *C07D 493/00* (2006.01)
- *C07D 401/00* (2006.01)
- *C07D 405/00* (2006.01)

(52) U.S. Cl. .................. 549/510; 549/511; 546/196; 546/207; 514/449

(58) Field of Classification Search ............... 546/196, 546/207; 549/214, 510, 511; 514/449
See application file for complete search history.

(56) References Cited

U.S. PATENT DOCUMENTS

| | | |
|---|---|---|
| 4,526,718 A | 7/1985 | Ross et al. |
| 4,680,391 A | 7/1987 | Firestone et al. |
| 4,814,470 A | 3/1989 | Colin et al. |
| 4,857,653 A | 8/1989 | Colin et al. |
| 4,876,399 A | 10/1989 | Holton et al. |
| 4,924,011 A | 5/1990 | Denis et al. |
| 4,924,012 A | 5/1990 | Colin et al. |
| 5,015,744 A | 5/1991 | Holton |
| 5,059,699 A | 10/1991 | Kingston |
| 5,136,060 A | 8/1992 | Holton |
| 5,175,315 A | 12/1992 | Holton |
| 5,229,526 A | 7/1993 | Holton |
| 5,243,045 A | 9/1993 | Holton et al. |
| 5,272,171 A | 12/1993 | Ueda et al. |
| 5,274,124 A | 12/1993 | Holton |
| 5,284,864 A * | 2/1994 | Holton et al. ............... 514/449 |
| 5,646,176 A | 7/1997 | Golik et al. |

FOREIGN PATENT DOCUMENTS

| | | |
|---|---|---|
| EP | 400971 | 12/1990 |
| EP | 414610 | 2/1991 |
| EP | 495718 | 7/1992 |
| EP | 534707 | 3/1993 |
| EP | 534708 | 3/1993 |
| EP | 534709 | 3/1993 |
| EP | 537905 | 4/1993 |
| EP | 569281 | 11/1993 |
| WO | 90/10443 | 9/1990 |
| WO | 93/06079 | 4/1993 |
| WO | 93/06094 | 4/1993 |

OTHER PUBLICATIONS

Lucatelli et al., Journal of Organic Chemistry, "Synthesis of C-3' Methyl Taxotere (Docetaxel)", vol. 67, pp. 9468-9470.*
D.H.R. Barton et al., J. Chem. Soc. Perkin Trans., Asymmetric Synthesis of 1,3,4-Trisubstituted and 3,4-Disubstituted 2-Azetidinones: Strategy Based on Use of D-Glucosamine as a Chiral Auxiliary in the Staudinger Reaction:, pp. 3211-3212, 1990.
B.C. Borer et al., Tetrahedron Letters, "An Asymmetric Synthesis of a 3-Hydroxy-β-Lactam by Ketene-Imine Cycloaddition: Utilization of Chiral Ketenes From Carbohydrates", vol. 32, No. 8, pp. 1039-1040, 1991.
R. Brieva et al., J. Org. Chem., "Chemoenzymatic Synthesis of the C-13 Side Chain of Taxol : Optically-Active 3-Hydroxy-4-Phenyl β-Lactam Derivatives" vol. 58, No. 5, pp. 1068-1075, 1993.
R.D.G. Cooper et al., Pure & Appl. Chem., "Chiral Control of the Staudinger Reaction", vol. 59, No. 3, pp. 485-492, 1987.

(Continued)

*Primary Examiner*—Thomas Mckenzie
*Assistant Examiner*—Niloofar Rahmani
(74) *Attorney, Agent, or Firm*—Elliott Korsen

(57) ABSTRACT

Novel β-lactams finding utility as intermediates in the preparation of sidechain-bearing taxanes such as taxol and taxol derivatives. The present invention also relates to novel methods of coupling β-lactams to form such sidechain-bearing taxanes, and to novel sidechain-bearing taxanes.

12 Claims, No Drawings

OTHER PUBLICATIONS

J-N. Denis et al., J. Am. Chem. Soc., "A Highly Efficient, Practical Approach to Natural Taxol", vol. 110, No. 17, pp. 5917-5919, 1988.

J-N. Denis et al., J. Org. Chem., "An Efficient, Enantioselective Synthesis of Taxol Side Chain", vol. 51, No. 1, pp. 46-50, 1986.

G.I. Georg et al., Tetrahedron Letters, "An Improved Method for the Steroselective Synthesis of β-Lactams from Carboxylic Acids and Imines", vol. 32, No. 5, p. 581-584, 1991.

G.I. Georg et al., Tetrahedron Letters, "Asymmetric Synthesis of β-Lactams and N-Benzoyl-3-Phenylisoserines Via the Staudinger Reaction", vol. 32, No. 27, pp. 3151-3154, 1991.

N.F. Magri et al., J. Org. Chem., "Modified Taxols. 3. Preparation and Acylation of Baccatin III", vol. 51, No. 16, pp. 3239-3242, 1986.

I. Ojiima et al., Tetrahedron, "New and Efficient approaches to the Semisynthesis of Taxol and its C-13 Side Chain Analogs by Means of β-Lactam Synthon Method", vol. 48, No. 34, pp. 6985-7012, 1992.

I. Ojiima et al., Tetrahedron Letters, "New and Efficient Routes to Norstatine and its Analogs with High Enantiomeric Purity by β-Lactam Synthon Methods", vol. 33, No. 39, pp. 5737-5740, 1992.

I. Ojima, et al., J. Org. Chem., "Efficient and Practical Asymmetric Synthesis of the Taxol C-13 Side Chain, N-Benzoyl-(2R,3S)-3-Phenylisoserine, and its Analogues via Chiral 3-Hydroxy-4-Aryl-β-Lactams Through Chiral Ester Enolate-Imine Cyclocondensation", vol. 56, No. 5., pp. 1681-1683, 1991.

C. Palomo et al., Tetrahedron Letters, "Highley Steroselective Synthesis of α-Hydroxy β-Amono Acids Through β-Amino Acids Through β-Lactams: Application to the Synethesis of the Taxol and Bestatin Side Chains and Related Systems", vol. 31, No. 44, pp. 6429-6432, 1990.

Greene, et al., "Protictive Groups in Organic Synthesis", 2nd Edition, 1991, pp. 10-12.

* cited by examiner

β-LACTAMS, METHODS FOR THE PREPARATION OF TAXANES, AND SIDECHAIN-BEARING TAXANES

CROSS-REFERENCE TO RELATED APPLICATIONS

This application claims priority to Ser. No. 10/006,599, filed on Dec. 5, 2001 now abandoned which is a continuation of Ser. No. 08/440,291, filed on May 12, 1995, now U.S. Pat. No. 6,350,887, which is a divisional of U.S. Ser. No. 08/320,628, filed on Oct. 11, 1994, now abandoned, which is a continuation of U.S. Ser. No. 08/033,598, filed on Mar. 19, 1993, now abandoned, all of which are herein incorporated by reference.

FIELD OF THE INVENTION

The present invention relates to novel β-lactams. The β-lactams of the present invention find utility as intermediates in the preparation of sidechain-bearing taxanes such as taxol and taxol derivatives. The present invention also relates to novel methods of coupling β-lactams to form such sidechain-bearing taxanes, and to novel sidechain-bearing taxanes.

BACKGROUND OF THE INVENTION

Taxanes are diterpene compounds having utility in the pharmaceutical field. For example, taxol, a taxane having the structure:

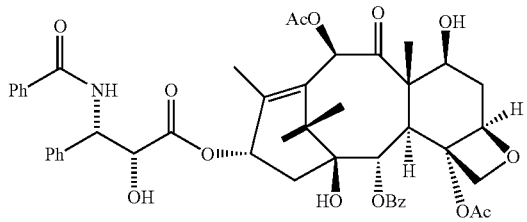

where Ph is phenyl, Ac is acetyl and Bz is benzoyl, has been found to be an effective anticancer agent.

Naturally occurring taxanes such as taxol may be found in plant materials, and have been isolated therefrom. Such taxanes may, however, be present in plant materials in relatively small amounts so that, in the case of taxol, for example, large numbers of the slow-growing yew trees forming a source for the compound may be required. The art has thus continued to search for synthetic, including semi-synthetic routes for the preparation of naturally occurring taxanes such as taxol, as well as routes for the preparation of synthetic, pharmaceutically useful analogs thereof.

SUMMARY OF THE INVENTION

The present invention provides novel β-lactam compounds of the following formula I:

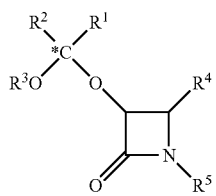

where
$R^1$ and $R^2$ are:
(i) both the same alkyl group;
(ii) together form a cycloalkyl group;
(iii) together form a cycloalkenyl group; or
(iv) together form a heterocyclo group;
$R^3$ is alkyl;
$R^4$ is aryl;
$R^5$ is hydrogen, arylcarbonyl, or alkyloxycarbonyl, and salts thereof.

The β-lactams of the present invention are useful as intermediates in the preparation of sidechain-bearing taxanes such as taxol and taxol derivatives. In particular, these compounds may be coupled with a taxane moiety to form the aforementioned sidechain.

As the stereochemistry of taxanes may affect their pharmaceutical activity, it is desirable to employ β-lactam intermediates which will provide the final taxane product with the stereochemistry sought. In the β-lactams of the present invention, the carbon marked with an asterisk in the above formula I is a non-asymmetric carbon. Where such a carbon center is asymmetric, a mixture of diastereomers can be formed. The β-lactams of the present invention provide superior results relative to β-lactams which contain an asymmetric carbon at the corresponding position since, when the latter compounds are prepared, or when they are coupled with a taxane moiety, products are formed as a mixture of stereoconfigurations. The formation of such a mixture of stereoisomers results in an inefficient use of the starting materials, and complicates separation and purification procedures.

The β-lactams of the formula I of the present invention are further advantageous in terms of the yield and purity of the final taxane product. In particular, the β-lactams of the present invention allow efficient conversion, and therefore use of lesser amounts, of starting materials, as well as simplified separation and purification procedures, when employed as intermediates in the preparation of sidechain-bearing taxanes.

The present invention also provides novel methods for using the aforementioned β-lactams of the formula I in the preparation of sidechain-bearing taxanes, and the novel sidechain-bearing taxanes prepared.

DETAILED DESCRIPTION OF THE INVENTION

The present invention is described further as follows.

The terms "alkyl" or "alk", as used herein alone or as part of another group, denote optionally substituted, straight and branched chain saturated hydrocarbon groups, preferably having 1 to 10 carbons in the normal chain. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include one or more of the following groups: halo, alkoxy, alkylthio, alkenyl, alkynyl, aryl, cycloalkyl, cycloalkenyl, hydroxy or protected hydroxy, carboxyl (—COOH), alkyloxycarbonyl, alkylcarbonyloxy, carbamoyl ($NH_2$—CO—), amino (—$NH_2$), mono- or dialkylamino, or thiol (—SH).

The terms "lower alk" or "lower alkyl", as used herein, denote such optionally substituted groups as described above for alkyl having 1 to 4 carbon atoms in the normal chain.

The terms "alkoxy" or "alkylthio", as used herein, denote an alkyl group as described above bonded through an oxygen linkage (—O—) or a sulfur linkage (—S—), respectively. The term "alkyloxycarbonyl", as used herein, denotes an alkoxy group bonded through a carbonyl group. The term "alkylcarbonyloxy", as used herein, denotes an alkyl group bonded through a carbonyl group which is, in turn, bonded through an oxygen linkage. The terms "monoalkylamino" or "dialkylamino" denote an amino group substituted by one or two alkyl groups as described above, respectively.

The term "alkenyl", as used herein alone or as part of another group, denotes such optionally substituted groups as described for alkyl, further containing at least one carbon to carbon double bond. Exemplary substituents include one or more alkyl groups as described above, or one or more groups described above as alkyl substituents.

The term "alkynyl", as used herein alone or as part of another group, denotes such optionally substituted groups as described for alkyl, further containing at least one carbon to carbon triple bond. Exemplary substituents include one or more alkyl groups as described above, or one or more groups described above as alkyl substituents.

The term "cycloalkyl", as used herein alone or as part of another group, denotes optionally substituted, saturated cyclic hydrocarbon ring systems, preferably containing 1 to 3 rings and 3 to 7 carbons per ring. Exemplary unsubstituted such groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The term "cycloalkenyl", as used herein alone or as part of another group, denotes such optionally substituted groups as described above for cycloalkyl, further containing at least one carbon to carbon double bond forming a partially unsaturated ring. Exemplary substituents include one or more alkyl groups as described above, or one or more groups described above as alkyl substituents.

The terms "ar" or "aryl", as used herein alone or as part of another group, denote optionally substituted, homocyclic aromatic groups, preferably containing 1 or 2 rings and 6 to 12 ring carbons. Exemplary unsubstituted such groups include phenyl, biphenyl, and naphthyl. Exemplary substituents include one or more, preferably three or fewer, nitro groups, alkyl groups as described above, or groups described above as alkyl substituents.

The term "arylcarbonyl", as used herein alone or as part of another group, denotes an aryl group as described above bonded through a carbonyl group.

The terms "heterocyclo" or "heterocyclic", as used herein alone or as part of another group, denote optionally substituted, fully saturated or unsaturated, aromatic or non-aromatic cyclic groups having at least one heteroatom in at least one ring, preferably monocyclic or bicyclic groups having 5 or 6 atoms in each ring. The heterocyclo group may, for example, have 1 or 2 oxygen atoms, 1 or 2 sulfur atoms, and/or 1 to 4 nitrogen atoms in the ring. Each heterocyclo group may be bonded through any carbon or heteroatom of the ring system. Exemplary heterocyclo groups include the following: thienyl, furyl, pyrrolyl, pyridyl, imidazolyl, pyrrolidinyl, piperidinyl, azepinyl, indolyl, isoindolyl, quinolinyl, isoquinolinyl, benzothiazolyl, benzoxazolyl, benzimidazolyl, benzoxadiazolyl, benzofurazanyl, and especially, tetrahydropyranyl (e.g. 4-tetrahydropyranyl). Exemplary substituents include one or more alkyl groups as described above, or one or more groups described above as alkyl substituents.

The terms "halogen" or "halo", as used herein alone or as part of another group, denote chlorine, bromine, fluorine, and iodine.

The term "taxane moiety", as used herein, denotes moieties containing the core structure:

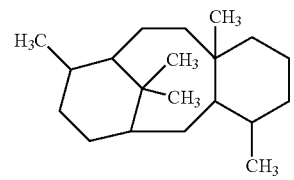

which core structure may be substituted and which may contain ethylenic unsaturation in the ring system thereof.

The term "taxane", as used herein, denotes compounds containing a taxane moiety as described above. The term "sidechain-bearing taxane", as used herein, denotes compounds containing a taxane moiety as described above, further containing a sidechain bonded to said moiety at C-13.

The term "hydroxy (or hydroxyl) protecting group", as used herein, denotes any group capable of protecting a free hydroxyl group which, subsequent to the reaction for which it is employed, may be removed without destroying the remainder of the molecule. Such groups, and the synthesis thereof, may be found in "Protective Groups in Organic Synthesis" by T. W. Greene, John Wiley and Sons, 1981, or Fieser & Fieser. Exemplary hydroxyl protecting groups include methoxymethyl, 1-ethoxyethyl, 1-methoxy-1-methylethyl, benzyloxymethyl, (β-trimethylsilylethoxy)methyl, tetrahydropyranyl, 2,2,2-trichloroethoxycarbonyl, t-butyl (diphenyl)silyl, trialkylsilyl, trichloromethoxycarbonyl, and 2,2,2-trichloroethoxymethyl.

The term "salt", as used herein, includes salts with organic and/or inorganic acids and/or bases.

The term "alkali metal silylamide base", as used herein, denotes a base containing the moiety:

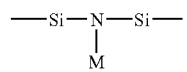

where M is an alkali metal such as lithium, sodium or potassium.

Preferred β-Lactams of the Formula I

Preferred β-lactams of the present invention are those compounds of the formula I which are crystalline compounds, rather than liquids (oils) at ambient conditions. Such crystalline compounds are advantageous relative to liquid compounds as they may be more easily prepared and obtained in pure form, particularly at larger scales, thus facilitating their subsequent use as intermediates in the formation of sidechain-bearing taxanes such as taxol and taxol derivatives.

Particularly preferred compounds of the formula I are those where $R^1$ and $R^2$ are both the same unsubstituted lower alkyl group, especially where $R^1$ and $R^2$ are both methyl; $R^3$ is unsubstituted lower alkyl, especially methyl; $R^4$ is phenyl; and $R^5$ is hydrogen, benzoyl or t-butoxycarbonyl.

Preparation of β-Lactams

β-lactams of the formula I may be prepared by methods such as those shown in the following Reaction Scheme for the prepartion of cis β-lactams of the formula I.

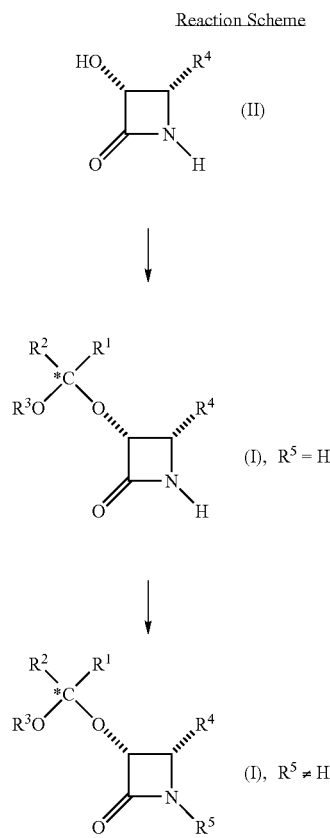

The starting compounds of the formula II may be prepared by methods such as those described in U.S. patent application Ser. No. 07/822,015, filed Jan. 15, 1992 by Patel et al., incorporated herein by reference. It is particularly preferred to employ β-lactams which are stereoisomerically (that is, enantiomerically) pure.

The compound of the formula II may be converted to a compound of the formula I by reaction of the former, in the presence of an acid catalyst, with a compound of the formula III or IV:

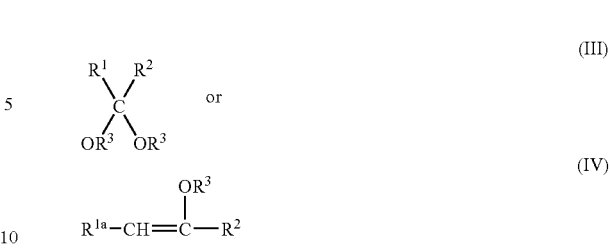

where $R^1$, $R^2$ and $R^3$ are as defined above and $R^{1a}$ (i) is a group such that $R^{1a}$—$CH_2$— is the same as $R^2$ when $R^2$ is alkyl or (ii) forms, together with $R^2$ and the atoms to which $R^{1a}$ and $R^2$ are bonded, a cycloalkenyl group or heterocyclo group containing at least one carbon to carbon double bond. Exemplary compounds of the formula III include the compounds: dimethoxypropane,

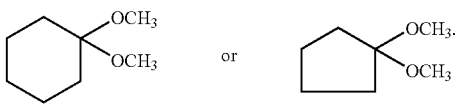

Exemplary compounds of the formula IV include the compounds:

A particularly preferred method for obtaining a compound of the formula I where $R^1$ and $R^2$ are both the same alkyl is by contacting a compound of the formula II with a compound of the formula IV where $R^3$ is as defined above and $R^{1a}$ is a group such that $R^{1a}$—$CH_2$— is the same as $R^2$, in the presence of an acid catalyst such as an organic sulfonic acid, for example, pyridinium p-toluene sulfonate (PPTS), toluene sulfonic acid or camphor sulfonic acid. 2-Methoxypropene is preferred as the compound of the formula IV.

The aforementioned reaction is preferably conducted at a temperature of from about −30° C. to about 30° C., especially at about 0° C., and at ambient pressure. The reaction may, for example, be completed over the course of about 0.5 hour to about 10 hours, and is preferably conducted under an atmosphere of inert gas such as argon.

Preferred mole ratios of the compound of the formula III or IV: the compound of the formula II are from about 6:1 to about 1:1. An amount of acid is employed which is effective to catalyze the reaction.

Organic solvents are preferably employed which are inert to the reaction. Particularly preferred solvents are acetone, dimethylformamide, tetrahydrofuran, dichloromethane, acetonitrile and toluene. Amounts of solvents are preferably those where the ratio of compound of the formula II: solvent is from about 1:5 to about 1:40, weight:volume.

The β-lactam of the formula I so obtained, where $R^5$ is hydrogen, may optionally be converted to a β-lactam of the formula I where $R^5$ is arylcarbonyl or alkyloxycarbonyl, with or without prior isolation of the β-lactam where $R^5$ is hydrogen, by contacting the former β-lactam where $R^5$ is hydrogen with a compound of the formula V or VI:

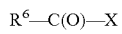 (V)

or

 (VI)

where
R⁶ is aryl or alkoxy; and
X is halo, especially chloro.

The above reaction is preferably conducted in the presence of a tertiary amine such as diisopropyl(ethyl)amine, triethylamine and 4-dimethylaminopyridine. Benzoyl chloride is preferred as the compound of the formula V, especially for the preparation of taxol. BOC anhydride (compound VI where R⁶ is t-butoxy) is preferred as the compound of the formula VI, especially for the preparation of taxotere.

In the above reaction, it is preferred to employ temperatures of from about −30° C. to about 30° C., especially about 0° C., and ambient pressure. The reaction may, for example, be completed over the course of about 2 hours to about 10 hours, and is preferably conducted under an atmosphere of inert gas such as argon.

Preferred mole ratios of the compound of the formula V or VI: β-lactam of the formula I where R⁵ is hydrogen are from about 1:1 to about 5:1. Preferred mole ratios of tertiary amine: β-lactam of the formula I where R⁵ is hydrogen are from about 1:1 to about 5:1.

Organic solvents are preferably employed which are inert to the reaction. Particularly preferred solvents are methylene chloride, tetrahydrofuran, acetonitrile, acetone, dimethylformamide and toluene. Amounts of solvents are preferably those where the starting β-lactam is from about 15% to about 80% by weight, based on the combined weight of solvent and starting β-lactam.

β-lactams where R⁵ is not hydrogen are preferred for use in the coupling methods described following.

Preparation of Sidechain-bearing Taxanes

Taxanes are diterpene compounds containing the taxane moiety:

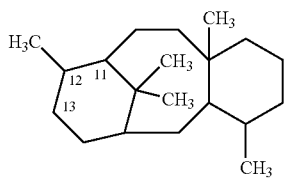

described above. Of particular interest are taxanes containing a taxane moiety in which the 11,12-positions are bonded through an ethylenic linkage, and in which the 13-position contains a sidechain, which taxanes are exemplified by taxol. Pharmacologically active taxanes such as taxol may be used as antitumor agents to treat patients suffering from cancers such as breast, ovarian, colon or lung cancers, melanoma and leukemia.

The present invention provides a novel method for the preparation of sidechain-bearing taxanes by coupling a β-lactam of the present invention to form said sidechain. In particular, the present invention provides a novel method for the preparation of a sidechain-bearing taxane of the following formula VII or a salt thereof:

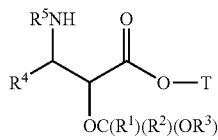 (VII)

where R¹, R², R³, R⁴ and R⁵ are as defined above, and T is a taxane moiety bonded directly at C-13 of said moiety;

comprising the step of contacting a β-lactam of the formula I or salt thereof of the present invention with a taxane compound of the following formula VIII or salt thereof:

HO-T (VIII)

where T is as defined above, in the presence of a coupling agent; and, optionally, converting the group —OC(R¹)(R²)(OR³) of said compound of the formula VII to hydroxyl, thereby forming a sidechain-bearing taxane or a salt thereof of the following formula IX:

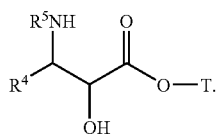 (IX)

The addition of a sidechain as described above, in and of itself, may impart an increased or more desirable pharmacological activity to the taxane product, or may form a taxane product which is more readily converted to a taxane having an increased or more desirable pharmacological activity than the starting compound. Exemplary taxanes which may be prepared by the present method for the preparation of a sidechain-bearing taxane include those compounds described in European Patent Publication No. 400,971, U.S. Pat. No. 4,876,399, U.S. Pat. No. 4,857,653, U.S. Pat. No. 4,814,470, U.S. Pat. No. 4,924,012, and U.S. Pat. No. 4,924,011, all incorporated herein by reference. It is preferred to prepare taxotere having the following structure:

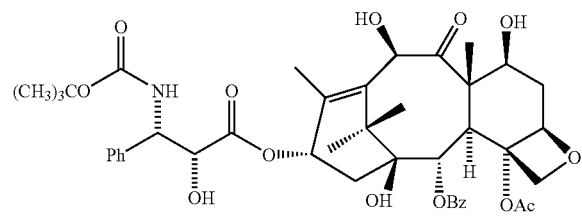

or, most preferably, taxol as the compound of the formula IX.

Exemplary compounds of the formula VIII, having the OH group bonded directly therein at C-13, which may be employed in the method of the present invention are described in the aforementioned documents incorporated by reference, especially in European Patent Publication No. 400,971. Most preferably, the compound of the formula VIII is a compound of the formula X:

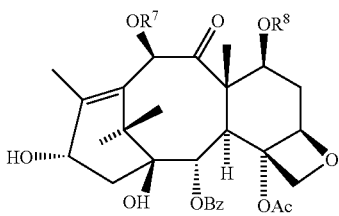 (X)

where
R[7] is hydrogen, alkylcarbonyl, or a hydroxyl protecting group, especially acetyl; and
R[8] is hydrogen or a hydroxyl protecting group; and particularly is a 7-O-trialkylsilyl baccatin III such as 7-O-triethylsilyl baccatin III or 7-O-trimethylsilyl baccatin III. 7-O-triethylsilyl baccatin III may, for example, be obtained from 10-deacetyl baccatin III as described by Denis et al., *J. Am. Chem. Soc.*, 110, 5917 (1988), incorporated herein by reference. 7-O-Triethylsilyl baccatin III is preferably prepared by the methods of the Examples herein. For example, ultimately, where R[7] is hydrogen, compound (X) may be acylated in situ before sidechain coupling.

The coupling agent employed in the method of the present invention may be any agent facilitating coupling to form the sidechain-bearing taxane of the formula VII, exemplified by tertiary amines such as triethyl amine, diisopropyl(ethyl) amine, pyridine, N-methyl imidazole, and 4-dimethylaminopyridine (DMAP), and metallic bases allowing formation of a C-13 metal alkoxide on the taxane of the formula VIII such as lithium diisopropylamide (LDA), unsubstituted lower alkyl lithium compounds, or phenyllithium.

Preferably, the coupling agent of the present method is an alkali metal silylamide base or a sterically hindered alkali metal amide base. Exemplary such bases are those of the formula XI:

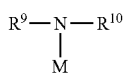 (XI)

where
R[9] and R[10] are trialkylsilyl, cycloalkyl, or together with the nitrogen atom to which they are bonded, form a heterocyclo group;

and
M is an alkali metal, such as lithium, sodium or potassium.

Preferred bases, particularly alkali metal silylamide bases of the formula XI, are those soluble in the reaction medium employed, and are most preferably an alkali metal hexamethyl disilazide (R[9] and R[10] are trimethylsilyl and M is sodium, lithium or potassium), especially lithium hexamethyldisilazide (LHMDS). "Sterically hindered alkali metal amide bases" include those bases containing the group —N(M)— where M is as defined above and which are substantially the same as, or more, sterically hindered than lithium hexamethyldisilazide in the coupling of a β-lactam to the C-13 hydroxyl group-containing taxane compound. Exemplary sterically hindered such bases include alkali metal tetramethyl piperidides and alkali metal dicyclohexylamides.

The aforementioned alkali metal bases, especially silylamide bases of the present method, are advantageous in that they are not strongly nucleophilic, so that degradation of the taxane starting material of the formula VIII is minimized or eliminated, and in that they provide a high yield (preferably, greater than or equal to about 90%) and purity (preferably greater than or equal to about 98%) of taxane product. The present invention further provides a method wherein a taxane of the formula VIII is coupled with any suitable β-lactam providing a sidechain at C-13 of said taxane, including but not limited to the β-lactams of the present invention, wherein an alkali metal silylamide base or a sterically hindered metal amide base is employed as a coupling agent for said coupling.

The above coupling method of the present invention is preferably conducted at a temperature of from about −70° C. to about 25° C., especially from about −30° C. to about 0° C., and at ambient pressure. The reaction may, for example, be completed over the course of about one-half hour to about four hours, and is preferably conducted under an inert atmosphere such as argon.

Preferred mole ratios of taxane starting compound of the formula VIII: β-lactam are those greater than about 1:1.6, most preferably from about 1:1 to about 1:1.3, especially about 1:1.2. Preferred mole ratios of taxane starting compound of the formula VIII: alkali metal base, such as silylamide base, are from about 1:1.1 to about 1:1.5, especially about 1:1.1.

Organic solvents are preferably employed which are inert to the reaction. Particularly preferred solvents are tetrahydrofuran (THF), toluene and ether. Amounts of solvents are preferably those where the ratio of starting taxane of the formula VIII to solvent is from about 1:1 to about 1:5, preferably 1:2.5, weight:volume.

The method of the present invention further comprises, subsequent to the reaction forming a sidechain-bearing taxane of the formula VII, optionally converting the group —OC(R[1])(R[2])(OR[3]) to hydroxyl. These groups may optionally be converted to a hydroxyl group sequentially or simultaneously with other hydroxyl protecting groups, such as those on the taxane moiety, by suitable means, such as by contact with an acid, for example, an inorganic acid such as HCl or HF, or organic acids such as acetic acid and the like.

Preferably, deprotection is conducted at a temperature of from about −30° C. to about 60° C., especially at about 0 to 25° C., and at ambient pressure. The reaction may, for example, be completed over the course of about 2 hours to about 72 hours, and is preferably conducted under an inert atmosphere such as argon.

Preferred mole ratios of acid for deprotection: taxane are from about 1:1 to about 20:1 (volume:weight). Organic solvents are preferably employed which are inert to the reaction. Particularly preferred solvents are an ethanol/tetrahydrofuran mixture or acetonitrile, acetone and water. Amounts of solvents are preferably those where the taxane is from about 1:10 to about 1:50, preferably 1:30, ratio of taxane: combined solvent, weight:volume (especially, tetrahydrofuran/ethanol and HCl/water).

The present invention also provides the novel sidechain-bearing taxanes of the formula VII and salts thereof described herein.

Taxol is preferably ultimately prepared as the sidechain-bearing taxane by the methods of the present invention. Taxol may be prepared, for example, by contacting a 7-O-trialkylsilyl baccatin III such as 7-O-triethylsilyl baccatin III, as the formula VIII compound, with (3R-cis)-1-benzoyl-3-(1-methoxy-1-methylethoxy)-4-phenyl-2-azetidinone, as the β-lactam, preferably in the presence of an alkali metal silylamide base. The triethylsilyloxy and 1-methoxy-1-methylethoxy groups may be converted to hydroxyl groups subsequent to sidechain formation, by deprotection methods such as those described above, to form taxol.

Salts or solvates such as hydrates of reactants or products may be employed or prepared as appropriate in any of the methods of the present invention.

As can be appreciated, the β-lactams and taxanes described herein may be present in more than one stereoisomeric form. All stereoisomers of the compounds described herein are contemplated, either alone (i.e., substantially free of other isomers), or in admixture with other selected (e.g. as a racemate) or all other stereoisomers. It is preferred that these compounds be substantially free of other isomers, that is, enantiomerically pure.

Preferred stereoconfigurations of the compounds of the formula I are those where the groups —OC(R$^1$) (R$^2$) (OR$^3$) and R$^4$ are in the cis position, that is,

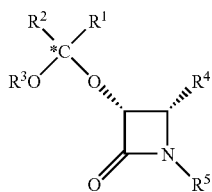

particularly where the compound of the formula I has the same absolute stereoconfiguration as the compound (3R-cis)-1-benzoyl-3-(1-methoxy-1-methylethoxy)-4-phenyl-2-azetidinone.

Preferred stereoconfigurations of the C-13 sidechains of the compounds of the formulae VII and IX correspond to the stereoconfiguration of the aforementioned cis β-lactams, that is,

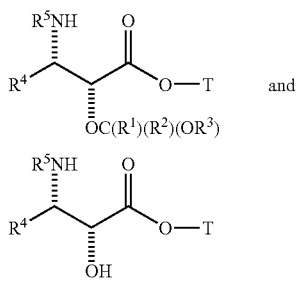

which sidechains have the same absolute stereoconfiguration as that of taxol.

The present invention is further described by the following examples which are illustrative only, and are in no way intended to limit the scope of the instant claims.

EXAMPLE 1

Preparation of (3R-cis)-3-(1-Methoxy-1-methylethoxy)-4-phenyl-2-azetidinone (a) (3R-cis)-3-Hydroxy-4-phenyl-2-azetidinone

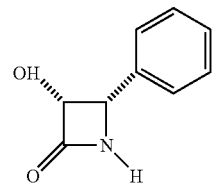

The title compound was prepared by enzymatic hydrolysis of racemic 3-acetyloxy-4-phenyl-2-azetidinone (see U.S. application Ser. No. 07/822,015, filed Jan. 15, 1992 by Patel et al.) to form (3R-cis)-3-acetyloxy-4-phenyl-2-azetidinone, followed by hydrolysis using base to form the optically active title compound.

(b) (3R-cis)-3-(1-Methoxy-1-methylethoxy)-4-phenyl-2-azetidinone

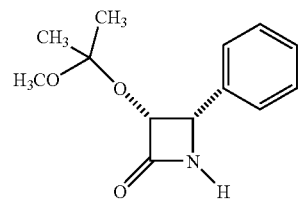

The product of step (a) above (8.49 g, 52.0 mmol) was added to a dry 500 ml 3-necked flask (dried in a 120° C. oven for ~12 hours and equipped with a magnetic stirbar and a digital thermometer), purged with argon, and dissolved in acetone (300 ml, freshly opened bottle of HPLC grade acetone; wt % H$_2$O (K.F.) <0.001). The yellowish solution was cooled to 0° (internal temperature was 1° C.). 2-Methoxypropene (15.0 ml, 156 mmol) (wt. % H$_2$O (K.F.) <0.001) was added dropwise over a period of 30 seconds. The internal temperature rose to ~2° C. during the addition of 2-methoxypropene. The resulting solution was stirred at 0° C. for 5 minutes before the addition of pyridinium p-toluene sulfonate (PPTS) (1.3 g, 5.2 mmol) (wt. % H$_2$O (K.F.) =0.001). After stirring at 0° C. for 30 minutes, TLC (thin layer chromatography) analysis revealed that the reaction was complete. (TLC analysis (silica gel, solvent: ethyl acetate, stain: phosphomolybdic acid/ethanol) of the crude reaction revealed a spot for the product (R$_f$=0.50) and no starting material (R$_f$=0.31)).

The solution was combined with ethyl acetate (250 ml), saturated aqueous NaHCO$_3$ (200 ml), and H$_2$O (100 ml) in a separatory funnel. After shaking the mixture and separating the layers, the aqueous fraction was extracted with ethyl acetate (3×100 ml). The combined organic fractions were washed with saturated aqueous NaCl (200 ml), dried over Na$_2$SO$_4$, filtered, and concentrated on a rotovap to give an off-white solid. All concentrations on the rotovap were conducted with a bath temperature of 35° C.

The crude product was dissolved in ethyl acetate (200 ml) and neutral activated charcoal (2 g) was added. The mixture was boiled gently for 5 minutes, cooled to room temperature, and suction filtered through a pad of Celite. Removal of the solvent on a rotovap as above, followed by exposure to high vacuum (~1 mm Hg for 45 minutes) gave 11.9 of an off-white solid. The solid was dissolved in boiling ethyl acetate (75 ml), and boiling hexanes (400 ml) were then added in 50 ml portions. The resulting cloudy solution was allowed to cool to room temperature. Crystallization began within ~1 minute after the solution was removed from the heat source. After standing at room temperature for 45 minutes, the mixture was chilled in a 4° C. cold room for 15 hours. The crystals were filtered, washed with 1:19 ethyl acetate/hexanes (3×100 ml) on a suction filter, and dried under high vacuum (~0.15 mm Hg for 20 hours) to give 9.55 g (78%) of the title product as off-white needles.

The mother liquor was concentrated on a rotovap as above, exposed to high vacuum (~1 mm Hg for 0.5 h.), and was then crystallized from ethyl acetate/hexanes to give 1.48 g (12%) of small off-white crystals of the title product. (The crystallization was performed in a similar manner as that for the first crop. The solid was dissolved in 5 ml of boiling ethyl acetate, and boiling hexanes (~40 ml) were added in ~5 ml portions until a few crystals appeared. Crystallization began immediately upon cooling to room temperature. The mixture was allowed to stand at room temperature for 1.5 h., then at 4° C. for 16 hours. The crystals were filtered, washed with 3×25 ml 1:19 ethyl acetate/hexanes on a suction filter, and dried under high vacuum (~0.2 mm Hg) for 24 hours).

For title product:

Elemental Analysis (%) $C_{13}H_{17}NO_3$

|   | Calcd. | Found |
|---|---|---|
| C | 66.36 | 66.30 |
| H | 7.28 | 7.40 |
| N | 5.95 | 6.04 |
| $H_2O$ (KF) | 0.00 | 0.00 | m.p. 136–137° C.

$[\alpha]^{22}_D$: +6.7° (c 1.0, $CHCl_3$).

$[\alpha]^{22}_{365}$: +93.3° (c 1.0, $CHCl_3$).

TLC: $R_f$=0.47 (silica gel, ethyl acetate) visualized by phosphomolybdic acid/ethanol.

EXAMPLE 2

Preparation of (3R-cis)-3-(1-Methoxy-1-methyl-ethoxy)-4-phenyl-2-azetidinone

The title product of step (a) of Example 1 above (30.1 g, 184 mmol, having a brownish color) was added to a flame-dried, argon-purged 500 mL flask (the flask was dried in a 120° C. oven for ~12 h. and was equipped with a magnetic stirbar and a digital thermometer), and dissolved in dimethylformamide (300 mL, wt. % $H_2O$ (K. F.)=0.05). The reddish-brown solution was cooled to 0° C. The internal temperature was 2° C. 2-Methoxypropene (53.0 mL, 553 mmol) was added dropwise over a period of 2 minutes (the internal temperature rose to ~2° C. during the addition of 2-methoxypropene), and the resulting solution was stirred at 0° C. for 5 minutes before the addition of pyridinium p-toluene sulfonate (PPTS, 4.6 g, 18.4 mmol). Approximately 5 minutes after the PPTS addition, the reaction temperature reached a maximum of 4.8° C. The solution became lighter in color as the reaction progressed. After stirring at 0° C. for 1 h, TLC analysis revealed that the reaction was complete. (TLC analysis (silica gel, solvent: ethyl acetate, stain: phosphomolybdic acid/ethanol) of an aliquot partitioned between ethyl acetate and $H_2O$ revealed a spot for the product ($R_f$=0.51) and no starting material ($R_f$=0.33)).

The solution was diluted with a 3:1 ethyl acetate/hexanes mixture (600 mL) and washed with half-saturated aqueous $NaHCO_3$ (500 mL). During the $NaHCO_3$ wash, most of the colored impurity was extracted into the aqueous phase. However, the organic phase remained a reddish-brown color. The aqueous fraction was extracted with ethyl acetate (2×150 mL). The combined organic fractions were washed with $H_2O$ (500 mL) (TLC analysis of the $H_2O$ wash showed no loss of the product to the aqueous layer), saturated aqueous NaCl (200 mL), dried over $Na_2SO_4$, filtered, and concentrated on a rotovap to give an off-white solid. All concentrations on the rotovap were conducted with a bath temperature of 40° C. The solid was dissolved in boiling ethyl acetate (180 mL), and hexanes (250 mL) were then added in ~20 mL portions until a few crystals appeared. The resulting solution was removed from the heat source and allowed to cool to room temperature. Extensive crystallization began within ~1 minute after the solution was removed from the heat source. After standing at room temperature for 1 h, the mixture was chilled in a 4° C. cold room for 17 h. The crystals were filtered, washed with 1:19 ethyl acetate/hexanes (3×150 mL) on a suction filter, and dried under high vacuum (~0.5 mm Hg for 22 h.) to give 32.6 g (75.4%) of the title product as fluffy white needles.

The mother liquor was concentrated on a rotovap as above, and was then crystallized from ethyl acetate/hexanes to give 6.25 g (14.4%) of the title product as fluffy white crystals. The crystallization was performed in a similar manner as that for the first crop. The solid was dissolved in 25 mL of boiling ethyl acetate, and hexanes (~60 mL) were added in ~5 mL portions until a few crystals appeared. Crystallization began immediately upon cooling to room temperature. The mixture was allowed to stand at room temperature for 1 h, then at 4° C. for 14 h. The crystals were filtered, washed with 3×100 mL 1:19 ethyl acetate/hexanes on a suction filter, and dried under high vacuum (~0.6 mm Hg) for 16 h. (Yield=90%).

Elemental Analysis (%) $C_{13}H_{17}NO_3$

|   | Calcd. | Found |
|---|---|---|
| C | 66.36 | 66.40 |
| H | 7.28 | 7.20 |
| N | 5.95 | 5.68 |
| $H_2O$ (KF) | 0.00 | 0.00 | m.p.=141° C.

$[\alpha]^{22}_D$: +6.5° (c 1.0, $CHCl_3$).

$[\alpha]^{22}_{365}$: +95.0° (c 1.0, $CHCl_3$). TLC: $R_f$=0.47 (silica gel, ethyl acetate) visualized by phosphomolybdic acid/ethanol.

The following alternative procedures were employed to prepare the title product:

(1) A mixture of the title product of step (a) of Example 1 (79.7 mg, 0.488 mmoles), dimethoxy propane (0.3 ml, 2.44 mmol), PPTS (about 12 mg, 0.049 mmol) and dimethylformamide (2 ml) under argon were stirred for 3 hours at about 0° C. and then for 24 hours at about 4° C. The product obtained was extracted with ethyl acetate and worked up (diluted with 10 ml ethyl acetate, washed with 0.5 saturated aqueous NaHCO$_3$; aqueous fraction extracted with 2×5 ml ethyl acetate; combined organic fractions were washed with 1×10 ml water, 10 ml saturated aqueous NaHCO$_3$, dried over Na$_2$SO$_4$, filtered and concentrated) to obtain quantitive yield of products, which was a 1:1.7 mixture of starting material and the title product (determined by TLC analysis).

(2) The title product was obtained by adding the title product of step (a) of Example 1 (92.5 mg) to an oven-dried 5 ml flask, purged with argon, diluted with dimethylformamide (1.5 ml) and cooled to 0° C. Dimethoxy propane (0.18 g) was added, followed by PPTS (14 mg). The solution was stirred at 0° C. for 5 hours, and worked up as above (yielding about 1:1.1 starting material to title product).

(3) The title product was obtained by adding the title product of step (a) of Example 1 (89.4 mg) to an flame-dried, argon-purged flask, dissolved in acetone (3.5 ml) and cooled to 0° C. Dimethoxy propane (0.17 g) was added, followed by PPTS (14 mg). The solution was stirred at 0° C. for 3 hours, transferred to a 4° C. cold room for 24 hours, and worked up to yield the title product in about a 8:2:1 starting material to title product to impurity ratio.

EXAMPLE 3

Preparation of (3R-cis)-1-Benzoyl-3-(1-methoxy-1-methylethoxy)-4-phenyl-2-azetidinone

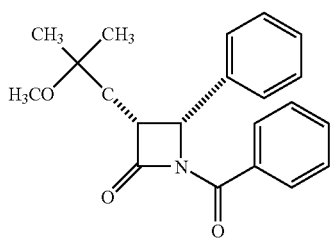

The title product of step (b) of Example 1 above (8.69 g, 36.9 mmol) was added to a dry 250 mL 3-necked flask (dried in a 120° C. oven for 24 hours and equipped with a magnetic stirbar and a digital thermometer), purged with argon and dissolved in CH$_2$Cl$_2$ (90 mL) (wt. % H$_2$O (K.F) <0.05). Diisopropyl(ethyl)amine (i-Pr$_2$NEt, 7.10 mL, 40.6 mmol) (wt. % H$_2$O (K.F.)=0.016) was added over a period of 30 seconds and then 4-dimethylaminopyridine (0.90 g, 7.4 mmol) (wt. % H$_2$O (K.F.) <0.05) was added in one portion. The resulting solution was cooled to 0° C. (the internal temperature was measured at 1° C.) and benzoyl chloride (4.70 mL, 40.6 mmol) was then added dropwise over a period of 7 minutes. The internal temperature rose to 8° C. during the addition. A slightly cloudy solution was obtained after the addition, which became a clear yellowish solution upon stirring at 0° C. The solution was then stirred at 0° C. for 1.5 h, at which time TLC analysis showed the reaction to be complete. (TLC analysis (silica gel, solvent: ethyl acetate, stain: phosphomolybdic acid/ethanol) of the crude reaction revealed a spot for the product (R$_f$=0.61) and no starting material (R$_f$=0.49).)

The solution was diluted with CH$_2$Cl$_2$ (150 mL), washed with saturated aqueous NaHCO$_3$, and the two layers were separated. The aqueous layer was extracted with CH$_2$Cl$_2$ (75 mL). The combined organic layers were washed with 5.7% aqueous NaH$_2$PO$_4$ (300 mL; measured pH of 5.7% aqueous NaH$_2$PO$_4$=4.25±0.05; measured pH of the resulting washing=5.57±0.05), saturated aqueous NaCl (100 mL), dried over Na$_2$SO$_4$, filtered, and concentrated on a rotovap to give an off-white foam. All concentrations on the rotovap were conducted with a bath temperature of 35° C. The crude product was dissolved in ethyl acetate (150 mL) and neutral activated charcoal (2 g) was added. The resulting mixture was boiled gently for 5 minutes, cooled to room temperature, and suction-filtered through a pad of Celite. The solution was considerably less colored than before the charcoal treatment. Removal of the solvent on a rotovap as above, followed by trituration of the resulting foam with hexanes (50 mL) gave a slurry of the solid product.

The slurry was concentrated on a rotovap as above and exposed to vacuum (~2 mm Hg for 15 minutes) to give 12.2 g of an off-white solid. The solid was dissolved in hot ethyl acetate (7 mL) and hot hexanes (~45 mL) were added in ~2 mL portions. This crystallization was conducted carefully to avoid having the product oil out. The resulting cloudy solution was then removed from the heat source. After a few minutes of cooling, a seed crystal was added and crystallization began within 10 minutes. After 1 hour at room temperature, the mixture was placed in a 4° C. cold room for 4 hours. The crystals were then filtered, washed with 1:19 ethyl acetate/hexanes (3×50 mL) on a suction filter, and dried under high vacuum (~0.2 mm Hg for 16 hours) to give 9.23 g (73.7%) of the title product as off-white crystals. The mother liquor contained additional product (by TLC analysis), but a second crop was not crystallized.

Elemental Analysis (%) C$_{20}$H$_{21}$NO$_4$.H$_2$O

|  | Calcd. | Found |
| --- | --- | --- |
| C | 70.41 | 70.14 |
| H | 6.26 | 6.10 |
| N | 4.11 | 4.13 |
| H$_2$O (KF) | 0.53 | 0.55 | m.p. 89–94° C.

$[\alpha]^{22}_D$: +173.1° (c 1.0, CHCl$_3$).

TLC: R$_f$=0.58 (silica gel, ethyl acetate) visualized by phosphomolybdic acid/ethanol.

EXAMPLE 4

Preparation of [2aR-[2aα,4β,4aβ,6β,9α(αR*,βS*),11α,12α,12aα,12bα]]-β-(Benzoylamino)-α-(1-methoxy-1-methylethoxy)hydroxybenzenepropanoic acid,6,12b-bis(acetyloxy)-12-(benzoyloxy)-2a,3,4,4a,5,6,9,10,11,12,12a,12b-dodecahydro-4-triethylsilyloxy-11-hydroxy-4a,8,13,13-tetramethyl-5-oxo-7,11-methano-1H-cyclodeca[3,4]benz[1,2-b]oxet-9-yl-ester (a) 7-TES Baccatin III

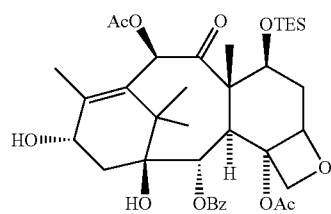

As used herein, Ac is acetyl, Bz is benzoyl and TES is triethylsilyl.

(i) [2aR-(2aα,4β,6β,9α,11β,12α,12aα,12bα)]-Benzoic acid, 12b-acetyloxy-2a,3,4,4a,5,6,9,10,11,12, 12a,12b-dodecahydro-6,9,11-trihydroxy-4a,8,13,13-tetramethyl-5-oxo-4-[(triethylsilyl)oxy]-7,11-methano-1H-cyclodeca[3,4]benz[1,2-b]oxet-12-yl ester (7-O-TES-10-Desacetylbaccatin III)

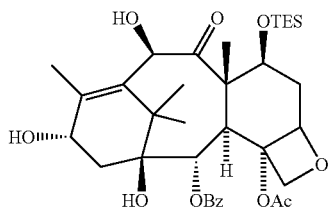

10-Desacetylbaccatin III (27.4 g, 50. 3 mmol) (amount not corrected for impurities measured (twice) as: $H_2O$: 1.0% (1.57%), $CH_3OH$: 1.49% (1.6%), ethyl acetate: 0.1% (0.09%), hexane (0.03%)) and 4-dimethylaminopyridine (2.62 g, 21.4 mmol) (wt. % $H_2O$ (K.F.)=0.09) were added to a flame-dried, argon purged 1 L 3-necked flask (equipped with a mechanical stirrer and a digital thermometer) and were dissolved in dry dimethylformamide (122 ml) (wt. % $H_2O$ (K.F.)=<0.01). $CH_2Cl_2$ (256 ml) (wt. % $H_2O$ (K.F.)=<0.01) was added and the resulting homogeneous solution was cooled to −50° C. (The temperature of the reaction solution rose from 23° C. to 25° C. during the addition of $CH_2Cl_2$.) Triethylamine ($NEt_3$, 16 ml, 120 mmol) (wt. % $H_2O$ (K.F.)=0.08) was added dropwise over 3 minutes and the resulting solution was stirred at −50° C. for 5 minutes before the dropwise addition of neat triethylsilyl chloride ($Et_3SiCl$, 18.6 ml, 111 mmol). The addition of $Et_3SiCl$ was conducted over a period of 10 minutes and the temperature of the reaction did not rise above −50° C. The reaction became very cloudy during the addition of $Et_3SiCl$. The resulting mixture was stirred at ∼−50° C. for 1 hour and was then allowed to stand (without stirring) in a −48° C. freezer for 22 hours. (A separate experiment showed that stirring the reaction at −48° C. for 8 hours resulted in ∼60% conversion.) The mixture was then removed from the freezer and warmed to ∼−10° C. (TLC analysis of the mixture (solvent: ethyl acetate, stain: phosphomolybdic acid/ethanol) revealed the absence of starting material and showed a single spot for the product (Rf=0.60).) The cold mixture was combined with EtOAc (1 L) and washed with $H_2O$ (890 ml). The resulting aqueous layer was separated and extracted with EtOAc (250 ml). The combined organic layers were washed with 5.7% aqueous $NaH_2PO_4$ (2×250 ml) (measured pH of 5.7% aqueous $NaH_2PO_4$=4.30±0.05; measured pH of the combined $NaH_2PO_4$ washings=5.75±0.05), half-saturated aqueous NaCl (250 ml), saturated aqueous NaCl (250 ml), dried over $Na_2SO_4$, filtered and concentrated on a rotovap. (All concentrations on the rotovap were conducted with a water bath temperature of 35° C.) The resulting semi-solid was further dried by exposure to high vacuum (∼1 mm Hg for 20 minutes) to give 41.5 g of a white solid. The crude product was then dissolved in $CH_2Cl_2$ (400 ml) (heating in a 35° C. water bath was required to dissolve the solid) and the volume of the resulting solution was reduced to ∼150 ml on a rotovap. Crystallization started immediately and the mixture was allowed to stand at room temperature for 1 hour. Hexanes (100 ml) were added and the mixture was gently swirled. The mixture was allowed to stand in a 4° C. cold room for 16.5 hours. The solid was filtered, washed with 1:9 $CH_2Cl_2$/hexanes (3×250 ml) on a suction filter, and dried under high vacuum (∼0.2 mm Hg for 42 hours) to give 26.1 g (79%) of the title product as a white powder. The mother liquor was concentrated on a rotovap and the residue crystallized from $CH_2Cl_2$ to give 4.5 g (14%) of the title product as white crystals. Recrystallization was conducted in the same manner as with the first crop of product: the solid was dissolved in $CH_2Cl_2$ (100 ml) without heating and the volume of the resulting solution was reduced to ∼7 ml on a rotovap. Crystallization began within 5 minutes. The mixture was allowed to stand at room temperature for 1 hour, then in a 4° C. cold room for 42 hours. The crystals were filtered, washed with 1:9 $CH_2Cl_2$/hexanes (3×50 ml) on a suction filter, and dried under high vacuum (∼0.2 mm Hg for 18 hours.). The $^1H$ NMR of this crop was identical to the $^1H$ NMR of the first crop of product.

The combined yield for the two crops was 93% (uncorrected).

Elemental Analysis (%) $C_{35}H_{50}O_{10}Si$

| | Calcd. | Found |
|---|---|---|
| C | 63.80 | 63.43 |
| H | 7.65 | 7.66 |
| $KF(H_2O)$ | 0.00 | 0.00 | mp: 239–242° C. (decomp.).

$[\alpha]^{22}{}_D$: −53.6° (c 1.0, $CHCl_3$).

TLC: $R_f$=0.60 (silica gel, EtOAc); visualized by phosphomolybdic acid/ethanol.

An alternative procedure was employed as follows:

In a flame-dried 250 ml 3-necked flask equipped with an argon inlet was placed 10-desacetyl-baccatin III (5.44 g, 10 mmol, having a water content of 1.56 wt. % and a methanol content of 1.6 wt %), 4-dimethylaminopyridine (0.49 g, 4 mmol) and N,N-dimethylformamide (24 ml, dried over 4 Å molecular sieve). The mixture was stirred at room temperature until homogeneous. Dichloromethane (50 ml, HPLC grade, used without purification) was added and the temperature was lowered to ∼50° C. Triethylamine (2.9 ml, 21 mmol) was added dropwise over a 5 minute period, followed by triethylsilylchloride (3.4 ml, 20 mmol) over a 10 minute period. The mixture was allowed to stand at −48° C. for a period of 21 hours, diluted with 200 ml of ethyl acetate and 175 ml of water. (The reaction was monitored by TLC using EtOAc as eluent: $R_f$ for the starting material=0.56, $R_f$ for the product=0.83; UV and PMA visualization.) The aqueous layer was separated and extracted with ethyl acetate (50 ml×1). The organic layers were combined and washed with 5% aqueous potassium phosphate mono basic (50 ml×2) (pH of 5% $KH_2PO_4$ in $H_2O$ was 4.3), half-saturated sodium chloride (50 ml×1), brine (50 ml×1), dried over sodium sulfate and concentrated in vacuo to give crude title product as a solid (7.45 g). The crude material was dissolved in 75 ml of hot dichloromethane and the total volume was reduced to 30 ml by heating to begin crystallization. It was set aside at room temperature for 2 hours and 4° C. for 16 hours. The crystals were filtered on a buchner funnel, washed with cold 10% dichloromethane in hexane (25 ml) and dried in vacuo to afford 5.38 g of title product. The mother liquors and washings were concentrated in vacuo and the solid residue was crystallized by dissolving in 8 ml of dichloromethane. Following the above crystallization procedure, 0.72 g of the product was obtained as a second crop. The combined yield of the title product 7-TES-10-desacetyl baccatin III, as a white solid, m.p. 238–240° C. was 6.10 g (93%).

Elemental Analysis (%) $C_{35}H_{50}O_{10}Si$

|   | Calcd. | Found |
|---|---|---|
| C | 63.80 | 63.76 |
| H | 7.65 | 7.66 | mp: 239–242° C.
$[\alpha]_D$: −53.7 (c 1.0, $CHCl_3$).
TLC: $R_f$=0.53 (silica gel, 50% EtOAc in hexane); UV and PMA visualization. HI=98.9%

(ii) [2aR-(2aα-4β,4aβ,6β,9α,11β,12α,12aα,12bα)]-6,12b-Bis(acetyloxy)-12-(benzoyloxy)-2a,3,4,4a,5,6,9,10,11,12,12a,12b-dodecahydro-9,11-dihydroxy-4a,8,13,13-tetramethyl-4-[(triethylsilyl)oxy]-7,11-methano-1H-cyclodeca[3,4]benz[1,2-b]oxet-5-one (7-O-TES-baccatin III)

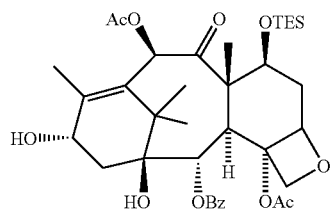

7-O-TES-10-desacetylbaccatin III prepared in step (i) above (21.4 g, 32.4 mmol) was added to a flame-dried, argon purged 1 L 3-necked flask (equipped with a mechanical stirrer and a digital thermometer) and dissolved in THF (350 ml, freshly distilled from sodium/benzophenone). The resulting solution was cooled to −70° C. A solution of n-butyllithium (n-BuLi, 14.6 ml of a 2.56 M solution in hexanes, 37.3 mmol, titrated in triplicate with diphenylacetic acid in THF at 0° C.) was added dropwise over a period of 23 minutes. The temperature of the reaction did not rise above −68° C. during the addition. Solids were formed upon the addition of n-BuLi and did not appear to dissolve at −70° C. The resulting mixture was stirred at −70° C. for 20 minutes and was then warmed to −48° C. (A clear homogeneous solution was obtained upon warming to −48° C.) After stirring at −48° C. for ½ hour, acetic anhydride (4.6 ml, 49 mmol, distilled (137–138° C., 1 atm) under an atmosphere of argon before use) was added dropwise over 7 minutes. The temperature of the reaction did not rise above −45° C. during the addition. The resulting solution was stirred at −48° C. for 20 minutes and then at 0° C. for 1 hour. The solution was diluted with ethyl acetate (350 ml), washed with saturated aqueous $NH_4Cl$ (250 ml), and the layers were separated. The aqueous layer was extracted with ethyl acetate (200 ml). The combined organic layers were washed with saturated aqueous NaCl, dried over $Na_2SO_4$, filtered, and concentrated on a rotovap. (All concentrations on the rotovap were conducted with a water bath temperature of 35° C.) Exposure of the semi-solid to high vacuum (~1.5 mm Hg for ½ hour) gave 24.7 g of a white solid. The crude product was dissolved in $CH_2Cl_2$ (300 ml) and the volume of the resulting solution was reduced to ~70 ml on a rotovap. Crystallization began within one minute. The mixture was allowed to stand at room temperature for 45 minutes, and then in a 4° C. cold room for 18 hours. The crystals were filtered, washed with 1:9 $CH_2Cl_2$/hexanes (3×100 ml) on a suction filter, and dried under high vacuum (~0.2 mm Hg for 19 hours) to give 20.9 g (92.0%) of the title product as fine white needles. The mother liquor was concentrated on a rotovap and the residue was crystallized from $CH_2Cl_2$/hexanes to give 0.82 g (3.6%) of the title product as small white crystals. Crystallization was conducted as follows: The residue was dissolved in $CH_2Cl_2$ (10 ml) and the volume of the resulting solution was reduced to ~5 ml on the rotovap. After standing at room temperature for ½ hour, no crystals had formed. Hexanes (5 ml) were added in 1 ml portions and solution was swirled. A few crystals were present by this time. The mixture was allowed to stand at room temperature for ½ hour (more crystals formed) and then in a 4° C. cold room for 18 hours. The crystals were filtered, washed with 1:9 $CH_2Cl_2$/hexanes on a suction filter, and dried under high vacuum (~0.15 mm Hg for 21 hours).

The combined yield for the two crops was 95.6%.
mp: 218–219° C. (decomp.).
$[\alpha]^{22}_D$: −78.4° (c 1.0, $CHCl_3$).
TLC: $R_f$=0.37 (silica gel, 1:9 acetone/$CH_2Cl_2$); visualized by phosphomolybdic acid/ethanol.

(b) [2aR-[2aα,4β,4aβ,6β,9α(αR*,βS*),11α,12α,12aα,12bα]]-β-(Benzoylamino)-α-(1-methoxy-1-methylethoxy)hydroxybenzenepropanoic acid, 6,12b-bis(acetyloxy)-12-(benzoyloxy)-2a,3,4,4a,5,6,9,10,11,12,12a,12b-dodecahydro-4-triethylsilyloxy-11-hydroxy-4a,8,13,13-tetramethyl-5-oxo-7,11-methano-1H-cyclodeca[3,4]benz[1,2-b]oxet-9-yl-ester

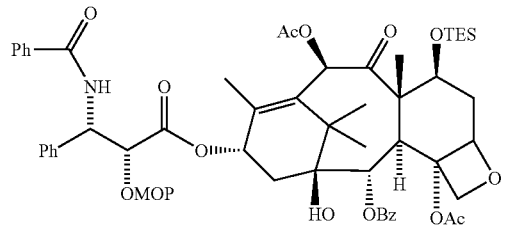

As used herein, Ph is phenyl, MOP is 1-methoxy-1-methylethyl, and THF is tetrahydrofuran.

To a solution of the compound prepared in step (a) above (50.00 g, 71.33 mmol) in THF (freshly distilled from sodium and benzophenone, 125 ml) at −50° C. (the cooling was applied only after the compound was completely dissolved in THF) was added dropwise with vigorous stirring lithium hexamethyldisilazide (LHMDS, 55.1 ml, 1.36 M in THF, 74.90 mmol; the reagent was titrated with 1,3-diphenylacetone p-tosylhydrazone) over a period of 20 minutes, so that the internal temperature did not rise above −48° C. After the addition the reaction mixture was warmed to −35° C. and stirred at that temperature for 5 minutes.

A freshly prepared solution of the compound prepared as the title product of Example 3 ("Compound 3") (27.85 g, 82.03 mmol) in THF (35 ml) was added dropwise to the reaction mixture over a period of 7 minutes. No significant exotherm was observed. The flask containing Compound 3 was washed with 5 ml of THF and the washing transferred to the reaction mixture. The resulting solution was brought to 0° C. by replacing the dry-ice bath with an ice-water bath and stirred for an additional 90 minutes. The reaction was monitored by TLC on reverse phase silica gel (EM Science RP-18 WF$_{254}$S) using acetonitrile/water (70/30) as eluent. R$_f$ for the title product was 0.31, for 7-TES-taxol (that is, the structure of taxol in which the 7-position hydroxyl group is replaced with TES-O—) 0.41, for 7-TES-baccatin III 0.47, for Compound 3, 0.63.

The reaction was quenched with a pH 7 phosphate buffer (50 ml), followed immediately by saturated NaHCO$_3$ (150 ml). It was diluted with ethyl acetate (EtOAc, 600 ml) and the layers were separated. The organic layer was dried over anhydrous Na$_2$SO$_4$, filtered and concentrated in vacuo to give the crude title product (82.3 g) as a pale yellow solid. The solid was dissolved in hot EtOAc (200 ml) and hexanes (110 ml) were added dropwise at the reflux temperature. The crystallization mixture was set aside at room temperature for 2 hours (upon cooling precipitation occurred rapidly), and then in a cold room for 7 hours. The solid was filtered and washed with a cold mixture of hexanes/EtOAc, 5/1 (2×80 ml). The resulting white crystals were dried on the suction filter for 1 hour, and then in vacuo (~0.6 mm Hg) overnight to give 67.37 g of the title product (91% based on 7-TES-baccatin III; $^1$H NMR showed 0.4 mol of EtOAc which gave a corrected yield of 87%) with an effective homogeneity index (HI) of 99.25% (95.73% title product and 3.52% 7-TES-taxol).

The mother liquor and the washings were combined and evaporated to dryness. The residue was dissolved in hot EtOAc (25 ml) and hexanes (40 ml) were added dropwise at the reflux temperature. After cooling to room temperature the mixture was set aside at room temperature for 1 hour, followed by 7 hours in the cold room. The solid was collected by filtration, dried on a suction filter and then in vacuo overnight (0.7 mm Hg) to yield 6.06 g (8%) of the title product with an effective HI of 96.6% (92.6% title product and 4.0% 7-TES-taxol.)

Elemental Analysis (%) C$_{57}$H$_{73}$NO$_{15}$Si.0.4 EtOAc

|   | Calcd. | Found |
|---|---|---|
| C | 65.44 | 65.49 |
| H | 7.14 | 7.44 |
| N | 1.30 | 1.47 | m.p. 153–155° C.

[α]$_D$: –59.6 (c 1, CHCl$_3$).

TLC: R$_f$=0.31 Reverse Phase HPTLC, acetonitrile/water, 70:30, UV visualization.

An alternative procedure for the preparation of 2'-MOP-7-triethylsilyl taxol was employed by the coupling of 7-O-TES baccatin III formed in situ as follows:

7-O-TES-10-desacetylbaccatin III (1.5177 mmol) was dissolved in 3.5 ml of dry tetrahydrofuran and cooled to –65 to –70° C. Lithium hexamethyldisilazide (LHMDS) was added dropwise (0.5 equivalents) and the mixture stirred for 20 minutes. Acetic anhydride (0.5 equivalents) was then added and the stirring was continued for the same period of time. The deprotection/acylation procedure was repeated three times (total 1.5 equivalents LHMDS and 2.0 equivalents acetic anhydride). Precipitation occured during anion formation (reaction mixture thickened), and the mixture was warmed up to 0° C. for 5 minutes.

Following cooling to –50° C. and further treatment dropwise with LHMDS, coupling with Compound 3 was conducted directly (by the procedure described above in step (b)). Yield: 851 mg (55%) from 7-O-TES-10-desacetylbaccatin III.

EXAMPLE 5

Preparation of [2aR-[2aα,4β,4aβ,6β,9α(αR*,βS*),11α,12α,12aα,12bα]]-β-(Benzoylamino)-α-(1-methoxy-1-methylethoxy)hydroxybenzenepropanoic acid,6,12b-bis(acetyloxy)-12-(benzoyloxy)-2a,3,4,4a,5,6,9,10,11,12,12a,12b-dodecahydro-4-triethylsilyloxy-11-hydroxy-4a,8,13,13-tetramethyl-5-oxo-7,11-methano-1H-cyclodeca[3,4]benz[1,2-b]oxet-9-yl ester (2'-MOP-7-triethylsilyl-taxol)

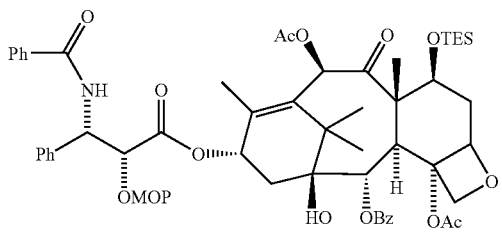

To a solution of 7-TES-baccatin III (5.00 g, 7.13 mmol) in THF (freshly distilled from sodium and benzophenone, 12.5 ml) at –50° C. (cooling was applied only after the compound was completely dissolved in THF) was added dropwise with vigorous stirring LHMDS (7.85 ml, 1.0 M in THF, 7.85 mmol), over a period of about 17 minutes, so that the internal temperature did not rise above –48° C. Close to the end of the addition a precipitate was formed, which made stirring difficult. An additional 1.5 ml of THF was added in order to allow efficient stirring. The reaction mixture was then warmed to –35° C. and stirred at that temperature for 10 minutes. The resulting cloudy solution at –35° C. was cooled back to –42° C. and then transferred dropwise to a solution of the azetidinone, Compound 3 (3.03 g, 8.92 mmol) in THF (2.5 ml) via a cannula. The temperature was kept between –19° C. and –10° C. during the addition, which took 7 minutes. The flask and the cannula were washed with THF (0.5 ml) and the washing was transferred to the reaction. At the end of the addition, the resulting solution was brought to 0° C. by replacing the dry-ice bath with an ice-water bath and stirred for an additional 75 minutes. The reaction was monitored by TLC on reverse phase silica gel (EM Science RP-18 WF$_{254}$S) using acetonitrile/water (70/30) as eluent. R$_f$ for the title product was 0.31, for 7-TES-taxol 0.41, for 7-TES-baccatin III 0.47.

The reaction was quenched with a pH 7 phosphate buffer (12 ml), followed immediately by saturated NaHCO$_3$ (30 ml). It was diluted with EtOAc (100 ml), the layers were separated, and the aqueous layer extracted with EtOAc (10 ml). The combined organic layers were dried over anhydrous Na$_2$SO$_4$, filtered and concentrated in vacuo to give the crude title product (9.13 g) as a tan solid. It was dissolved in hot EtOAc (20 ml) and hexanes (13 ml) were added dropwise at the reflux temperature. The solution was set aside at room temperature for 36 hours, and then in the cold room for 2 hours. The solid was filtered and washed with a cold mixture of hexanes/EtOAc, 5/1 (2×10 ml). (The mother liquor (1.52 g, effective HI 52.4) and the washings (0.32 g, effective HI 53.4) were collected separately and set aside.) The resulting white crystals were dried on the suction filter for 20 minutes, and then in vacuo (~0.5 mm Hg) overnight to give 6.59 g of the title product (89% based on 7-TES-baccatin III) with an effective HI of 99.3% (96.0% title product and 3.3% 7-TES-taxol).

Elemental Analysis (%) $C_{57}H_{73}NO_{15}Si$

|   | Calcd. | Found |
|---|--------|-------|
| C | 65.81  | 65.47 |
| H | 7.07   | 7.12  |
| N | 1.35   | 1.64  | m.p. 153–155° C.

$[\alpha]_D$: −59.6 (c 1, $CHCl_3$).

TLC: $R_f$=0.31 Reverse Phase HPTLC, acetonitrile/water, 70:30, UV visualization.

EXAMPLE 6

Preparation of Taxol [2aR-[2aα,4β,4aβ,6β,9α(αR*,βS*),11α,12α,12aα,12bα]]-β-(Benzoylamino)-α-hydroxy-benzenepropanoic acid, 6,12b-bis(acetyloxy)-12-(benzoyloxy)-2a,3,4,4a,5,6,9,10,11,12,12a,12b-dodecahydro-4-11-dihydroxy-4a,8,13,13-tetramethyl-5-oxo-7,11-methano-1H-cyclodeca[3,4]benz[1,2-b]oxet-9-yl-ester

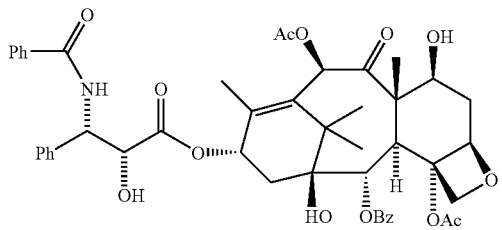

To a solution of the title product of Example 5 above ("Compound 5", 5.0 g, 4.81 mmol; HI 99.3% including Compound 5, HI 96.0 and 7-TES-taxol, HI 3.3) in ethanol (EtOH, 100 mL) and THF (80 mL) at 0° C. (Compound 5 was dissolved in EtOH/THF before cooling to 0° C. using an ice bath) was added precooled (~5° C.) 1.5 N HCl (aqueous, aq) dropwise with vigorous stirring over a period of 12 minutes. The cloudiness that appeared during the addition of 1.5 N HCl disappeared instantly. The resulting clear solution was stirred at 0° C. for 15 minutes and stored at 4° C. for 19.5 hrs. HPLC analysis of an aliquot (3μ Phenyl BD column; 35% $CH_3CN$/65% $H_2O$ linear gradient for 26 minutes; 100% $CH_3CN$ linear gradient for 7 minutes; 35% $CH_3CN$/65% $H_2O$ isocratic for 7 minutes) at this point indicated the presence of taxol (98.6%), 7-TES taxol (0.6%) and a polar impurity (0.3%) along with other minor impurities. The reaction mixture was diluted with ethyl acetate (EtOAc, 200 mL) and washed with cold (about 5° C.) $NaHCO_3$ (500 mL and 2×200 mL). Washing was continued until the pH of the aqueous washings was ~8.5.

The combined aqueous layer was extracted with EtOAc (2×100 mL). The organic layers were combined and washed with brine (300 mL), dried ($Na_2SO_4$, 100 g), filtered and concentrated to give crude taxol as a white solid (4.44 g; HPLC HI 97.7%). It was dissolved in 25 mL of methanol (MeOH)/isopropanol (IPA) (1:5.8) and diluted with $H_2O$ (1.4 mL) by gentle warming (warmed to ~40 to 45° C. on a water bath). The resulting solution was stored in a hexane atmosphere (the container having the solution of crude taxol in MeOH/IPA/$H_2O$ was placed in another larger container having hexane (20 ml) in a closed system at room temperature) at room temperature for 16 hrs. The white crystalline (visual examination under a microscope) solid was filtered, washed with cold (5° C.) hexane (25 mL) and dried under high vacuum to give 3.8 g (93.0%) of taxol with HPLC HI 99.0%. The mother liquor and the washings were concentrated under reduced pressure to give 0.28 g (7.0%) of a faint yellow solid (HPLC HI 80.6%) which was set aside for further processing at a later time.

Elemental Analysis (%) $C_{47}H_{51}NO_{14}$·1.0 $H_2O$

|          | Calcd. | Found |
|----------|--------|-------|
| C        | 64.74  | 64.71 |
| H        | 6.13   | 6.48  |
| N        | 1.61   | 1.57  |
| KF($H_2O$) | 2.07   | 1.90  | m.p. 211–213° C.

$[\alpha]_D$: −51.5 (c 1, $CHCl_3$).

TLC: $R_f$=0.22; MeOH:AcOEt:Hexane; 0.6:4.0:5.4; UV and PMA Visualization.

EXAMPLE 7

Preparation of Taxol

To a 2 L polyethylene bottle containing a solution of Compound 5 (2'-MOP-7-triethylsilyltaxol, 20 g, 19.1 mmol) in acetonitrile (800 ml) and pyridine (48 ml) at 0° C. was added dropwise 48% aqueous hydrofluoric acid (HF) (104 ml) over a 60 minute period. The internal temperature did not exceed 5° C. during the addition. The clear solution was held at 4° C. without agitation for a period of 24 hrs. The reaction was monitored by HPLC (Waters, Nova-Pak Phenyl, 3.9×150 mm column; absorption: 227 nm; flow rate: 2 ml/min)

Chromatography condition:

0–26 min, 35% $CH_3CN$/65% $H_2O$ to 100% $CH_3CN$, linear gradient, 26–28 min, 100% $CH_3CN$ to 35% $CH_3CN$/65% $H_2O$, linear gradient, 28–35 min, 35% $CH_3CN$/65% $H_2O$, isocratic Rt: 13.73 for 7-TES-taxol Rt: 6.65 for Taxol Rt: 4.96 for 10-desacetyl-taxol After 19 hrs of reaction, 0.36% of 7-TES-taxol remained in this mixture. After 24 hrs, 7-TES-taxol and 10-desacetyl-taxol were not present (impurity index II<0.04%) in the reaction mixture. The solution was then diluted with ethyl acetate (1 L) and washed with 1N HCl (800 ml×2). The combined aqueous layer was extracted with ethyl acetate (400 ml×1). The organic layers were combined and washed with saturated aqueous sodium bicarbonate solution (800 ml×5), brine (300 ml×1), dried over sodium sulfate, filtered and concentrated to give 17.46 g (~100%) of crude taxol as a white solid. The HPLC HI for the crude taxol obtained above was 98.7%. The yield is uncorrected.

Elemental Analysis (%) $C_{47}H_{51}NO_{14} \cdot 1.3\ H_2O$

|   | Calcd. | Found |
|---|---|---|
| C | 64.34 | 64.32 |
| H | 6.16 | 5.99 |
| N | 1.60 | 2.00 |
| KF(H$_2$O) | 2.67 | 2.00 | m.p. 207.5–212° C. (w/decomp).

$[\alpha]_D$: –52.5 (c 1, CHCl$_3$).

TLC: R$_f$=0.22; Silica gel; MeOH:AcOEt:Hexane; 0.6:4.0:5.4; UV and PMA Visualization.

EXAMPLE 8

Preparation of Taxol

To a solution of 2'-MOP-7-TES-taxol (Compound 5, 5.0 g, 4.81 mmol, HI 99.2% (including 2'-MOP-7-TES-taxol, HI 95.7) in ethanol (EtOH, 50 ml) and THF (40 ml) at 0° C. (ice bath, 2'-MOP-7-TES-taxol was dissolved in EtOH/THF before cooling to 0° C.) was added precooled (~5° C.) 1.5 N HCl (aq., 50 ml) dropwise with vigorous stirring over a period of 40 minutes. The cloudiness that appeared during the addition of 1.5 N HCl disappeared instantly. The resulting clear solution was stirred at –2° C. for 1 hour and stored at 4° C. for 22 hours. A white solid about 100–200 mg (taxol) precipitated at this stage. (In process HPLC analysis of an aliquot after 20 hours (3μ Phenyl BD column); 35% CH$_3$CN/65% H$_2$O-linear gradient for 26 minutes; 100% CH$_3$CN-linear gradient for 7 minutes; 35% CH$_3$CN/65% H$_2$O-isocratic for 7 minutes) at this point indicated the presence of taxol (97.2%), 7-TES taxol (0.2%), 10-desacetyl taxol (0.7%) with other minor impurities.) The reaction mixture was diluted with EtOAc (200 ml) and washed with cold (~5° C.) NaHCO$_3$ (400 ml and 2×200 ml). (The pH of the aqueous washings should preferably be ~8.5 (where not, washing is preferably continued until the pH reaches 8.5)). The combined aqueous layer was extracted with EtOAc (2×80 ml). The organic layers were combined and washed with brine (200 ml), dried (Na$_2$SO$_4$, 100 g), filtered and concentrated to give crude taxol as a white solid (4.2 g; HI 97.9%). It was dissolved in 31 ml of EtOH/heptane (6:4) and diluted with H$_2$O (0.15 ml) by gentle warming (warmed to ~30–35° C. on a water bath). The resulting homogenous clear solution was stored at 4° C. for about 20 hours. The white crystalline (visual examination under a microscope) solid was filtered, washed with cold (5° C.) heptane (20 ml) and dried under high vacuum to give 3.72 g (90.6%) of taxol with HI 98.6%. The mother liquour and the washings on concentration under reduced pressure gave crude taxol (0.45 g) which on crystallization (dissolved in EtOH/heptane (0.5:0.3, 4.6 ml) and H$_2$O (20 μl) and stored at 4° for 20 hours) yielded the second crop of white crystalline (visual examination under a microscope) solid (0.18 g; 4.0%; HI 92.0%).

Elemental Analysis (%) $C_{47}N_{51}NO_{14} \cdot 2.55\ H_2O$

|   | Calc. | Found |
|---|---|---|
| C | 62.73 | 62.35 |
| H | 6.28 | 6.43 |

-continued

|   | Calc. | Found |
|---|---|---|
| N | 1.56 | 1.94 |
| H$_2$O | 5.11 | 4.91 | mp=207–208° C.

Opt. rot.: $[\alpha]_D$=–52.3° (c 1, CHCl$_3$).

TLC: R$_f$=0.22; silica gel; MeOH:EtOAc:Hex, 0.6:4.0:5.4; UV and PMA visualization.

HPLC: HI=98.6%

What is claimed is:

1. A method for the preparation of a sidechain-bearing taxane of the following formula VII or a salt thereof:

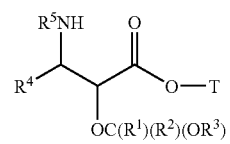

(VII)

where

R$^1$ and R2 are:
  (i) both the same alkyl group;
  (ii) together form a cycloalkyl group;
  (iii) together form a cycloalkenyl group; or
  (iv) together form a heterocyclo group;

R$^3$ is alkyl;

R$^4$ is aryl;

R$^5$ is hydrogen, arylcarbonyl, or alkyloxycarbonyl; and

T is a taxane moiety bonded directly at C-13 of said moiety;

comprising the step of contacting a β-lactam of the following formula I or a salt thereof:

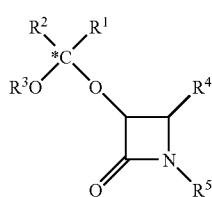

(I)

where R$^1$, R$^2$, R$^3$, R$^4$, and R$^5$ are as defined above with a taxane compound of the following formula VIII or a salt thereof:

HO-T     (VIII)

where T is as defined above, in the presence of a coupling agent; and optionally converting the group —OC(R$^1$)(R$^2$)(OR$^3$) of said compound of the formula VII to hydroxyl, thereby forming a sidechain bearing taxane or a salt thereof of the following formula IX:

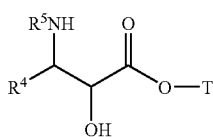

where $R^4$, $R^5$, and T are as defined above.

2. The method of claim 1, wherein the tax ane of the formula VIII is a taxane of the following formula X:

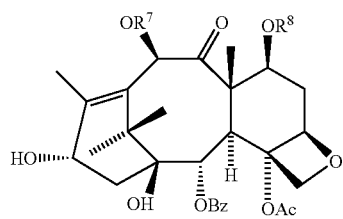

where
Bz is benzoyl;
Ac is acetyl;
$R^7$ is hydrogen, alkylcarbonyl, or a hydroxyl protecting group; and
$R^8$ is hydrogen or a hydroxyl protecting group.

3. The method of claim 2, wherein said taxane of the formula X is a 7-O-trialkylsilyl baccatin III.

4. The method of claim 1, where in said coupling agent is an alkali metal silylamide base or a sterically hindered alkali metal amide base.

5. The method of claim 4, wherein said coupling agent has the following formula XI:

where
$R^9$ and $R^{10}$ are trialkylsilyl, cycloalkyl, or together with the nitrogen atom to which they are bonded, for a heterocyclo group; and
M is an alkali metal.

6. The method of claim 5, wherein said coupling agent is an alkali metal hexamethyl disilazide.

7. The method of claim 6 wherein said alkali metal hexamethyl disilazide is lithium hexamethyl disilazide.

8. The method of claim 2, further comprising deprotection of one or more hydroxyl groups on the taxane moiety of the sidechain-bearing taxane formed.

9. The method of claim 8, wherein an acid is employed for said deprotection.

10. The method of claim 1, wherein $R^1$ and $R^2$ are both the same unsubstituted lower alkyl group, $R^3$ is unsubstituted lower alkyl, $R^4$ is phenyl, and $R^5$ benzoyl or t-butoxycarbonyl.

11. The method of claim 10, wherein taxol is prepared.

12. The method of claim 10, wherein taxotere is prepared.

* * * * *